(12) United States Patent
Umehara et al.

(10) Patent No.: US 10,199,589 B2
(45) Date of Patent: Feb. 5, 2019

(54) PHOTOELECTRIC CONVERSION ELEMENT AND IMAGE SENSOR USING SAME

(71) Applicant: TORAY INDUSTRIES, INC., Tokyo (JP)

(72) Inventors: Masaaki Umehara, Otsu (JP); Tsuyoshi Tominaga, Seoul (KR); Jinwoo Kwon, Seoul (KR)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/534,768

(22) PCT Filed: Dec. 18, 2015

(86) PCT No.: PCT/JP2015/085503
§ 371 (c)(1),
(2) Date: Jun. 9, 2017

(87) PCT Pub. No.: WO2016/111140
PCT Pub. Date: Jul. 14, 2016

(65) Prior Publication Data
US 2017/0309849 A1    Oct. 26, 2017

(30) Foreign Application Priority Data

Jan. 9, 2015 (JP) ................. 2015-002862

(51) Int. Cl.
*C07D 333/36* (2006.01)
*C07D 333/56* (2006.01)
(Continued)

(52) U.S. Cl.
CPC .......... *H01L 51/424* (2013.01); *C07D 333/36* (2013.01); *C07D 333/56* (2013.01);
(Continued)

(58) Field of Classification Search
CPC ... H01L 51/424; H01L 27/146; H01L 27/307; H01L 31/10; H01L 51/00; C07C 255/34;
(Continued)

(56) References Cited

U.S. PATENT DOCUMENTS 9,508,945 B2 * 11/2016 Holmes ............... H01L 51/4246
2011/0101325 A1    5/2011 Uetani et al.
(Continued)

FOREIGN PATENT DOCUMENTS

CN    102077368 A    5/2011
JP    2007-335760 A    12/2007
(Continued)

OTHER PUBLICATIONS

Schwaben et al., "Synthesis and Solid-State Structures of 6,13-Bis(trifluoromethyl)- and 6,13-Dialkoxypentacene", 2013, Eur. J. Org. Chem., 1639-1643.*
(Continued)

*Primary Examiner* — Tom Thomas
*Assistant Examiner* — Benjamin Tzu-Hung Liu
(74) *Attorney, Agent, or Firm* — Birch, Stewart, Kolasch & Birch, LLP

(57) ABSTRACT

A photoelectric conversion element, including a first electrode, a second electrode, and at least one organic layer being present between the first electrode and the second electrode, in which the organic layer contains at least two kinds of compounds having the same skeletons and different substituents in combination.

17 Claims, 3 Drawing Sheets

(51) Int. Cl.
| | |
|---|---|
| C07D 333/72 | (2006.01) |
| C07D 409/04 | (2006.01) |
| C07D 409/14 | (2006.01) |
| C09B 23/10 | (2006.01) |
| C09B 57/00 | (2006.01) |
| H01L 27/30 | (2006.01) |
| H01L 51/00 | (2006.01) |
| H01L 51/42 | (2006.01) |
| C07D 407/14 | (2006.01) |
| H01L 27/146 | (2006.01) |
| H01L 31/10 | (2006.01) |
| C07D 409/06 | (2006.01) |
| C07D 409/12 | (2006.01) |
| C07D 495/04 | (2006.01) |
| C07D 495/14 | (2006.01) |
| C07C 255/34 | (2006.01) |
| C07C 255/51 | (2006.01) |

(52) U.S. Cl.
CPC ......... *C07D 333/72* (2013.01); *C07D 407/14* (2013.01); *C07D 409/04* (2013.01); *C07D 409/06* (2013.01); *C07D 409/12* (2013.01); *C07D 495/04* (2013.01); *C07D 495/14* (2013.01); *C09B 23/105* (2013.01); *C09B 57/008* (2013.01); *H01L 27/146* (2013.01); *H01L 31/10* (2013.01); *H01L 51/006* (2013.01); *H01L 51/0052* (2013.01); *H01L 51/0053* (2013.01); *H01L 51/0054* (2013.01); *H01L 51/0055* (2013.01); *H01L 51/0056* (2013.01); *H01L 51/0061* (2013.01); *H01L 51/0068* (2013.01); *H01L 51/0073* (2013.01); *H01L 51/42* (2013.01); *H01L 51/4253* (2013.01); *C07C 255/34* (2013.01); *C07C 255/51* (2013.01); *H01L 27/307* (2013.01); *H01L 51/0046* (2013.01); *H01L 51/0072* (2013.01); *H01L 51/0074* (2013.01); *H01L 51/0078* (2013.01)

(58) Field of Classification Search
CPC .. C07C 255/51; C07D 333/36; C07D 333/56; C07D 333/72; C07D 407/14; C07D 409/04; C07D 409/06; C07D 409/12; C07D 495/04; C07D 495/14; C09B 23/105; C09B 57/008
See application file for complete search history.

(56) References Cited

U.S. PATENT DOCUMENTS

| | | | |
|---|---|---|---|
| 2011/0139969 A1* | 6/2011 | Nii | H01L 27/14621 |
| | | | 250/226 |
| 2012/0048377 A1 | 3/2012 | Winzenberg et al. | |
| 2014/0001455 A1 | 1/2014 | Holmes et al. | |

FOREIGN PATENT DOCUMENTS

| | | |
|---|---|---|
| JP | 2011-9622 A | 1/2011 |
| JP | 2012-519382 A | 8/2012 |

OTHER PUBLICATIONS

International Search Report for PCT/JP2015/085503 (PCT/ISA/210) dated Mar. 8, 2016.
Written Opinion of the International Searching Authority for PCT/JP2015/085503 (PCT/ISA/237) dated Mar. 8, 2016.
Chinese Office Action and Search Report for Application No. 201580072492.8, dated Jun. 25, 2018.

\* cited by examiner

[Fig. 1]
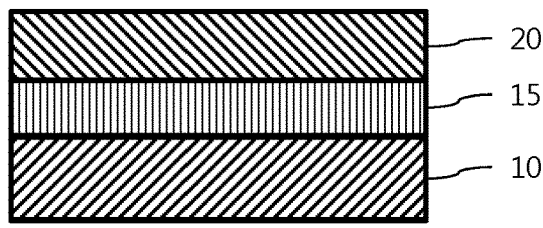
[Fig. 2]
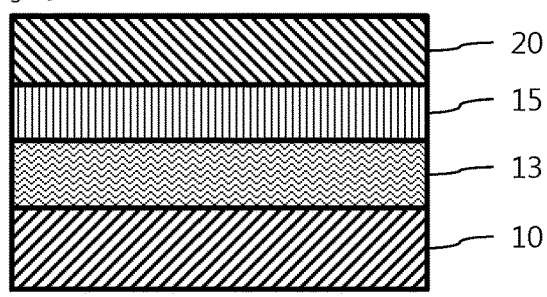
[Fig. 3]
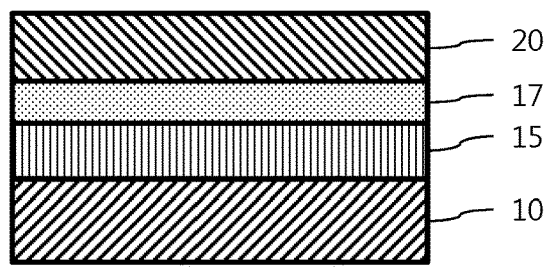
[Fig. 4]
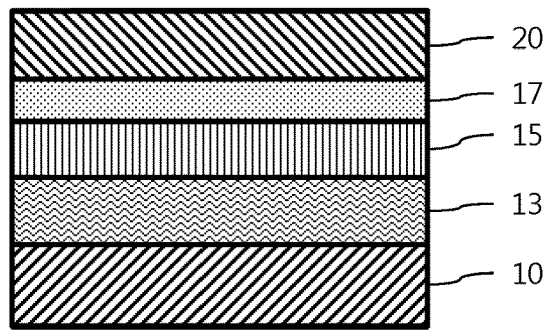

[Fig. 5]
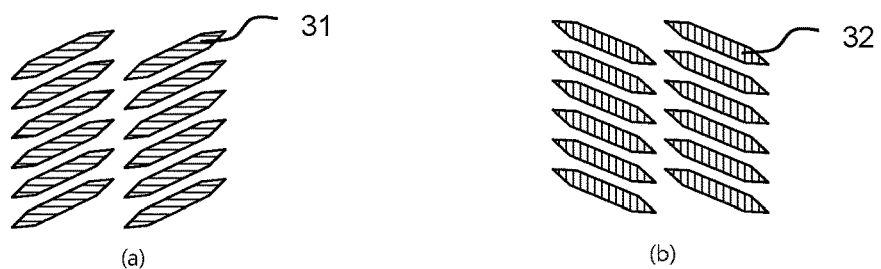
(a)          (b)
[Fig. 6]
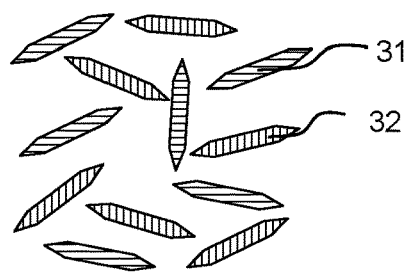
[Fig. 7]
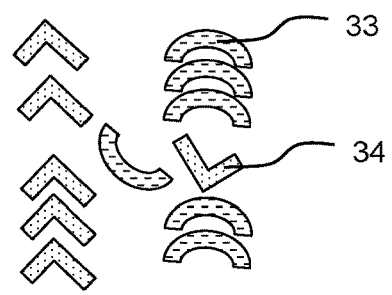
[Fig. 8]
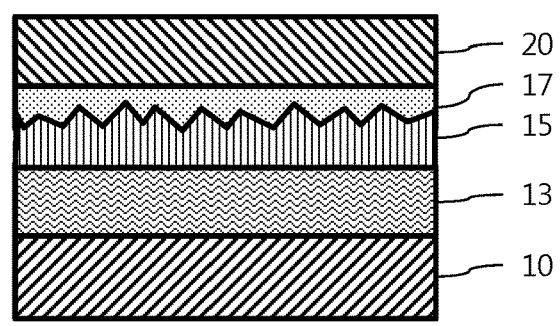

[Fig. 9]
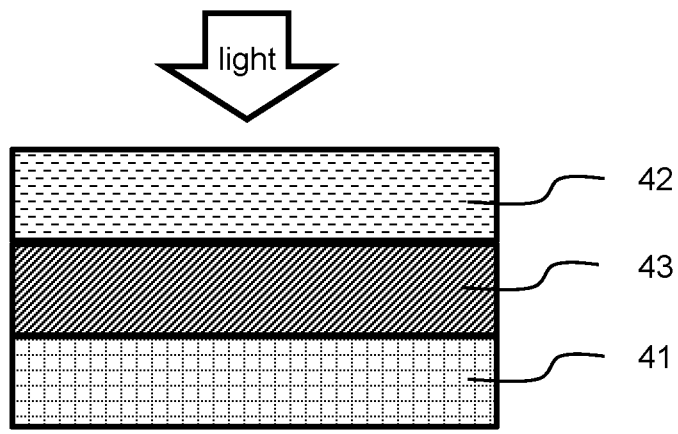
[Fig. 10]
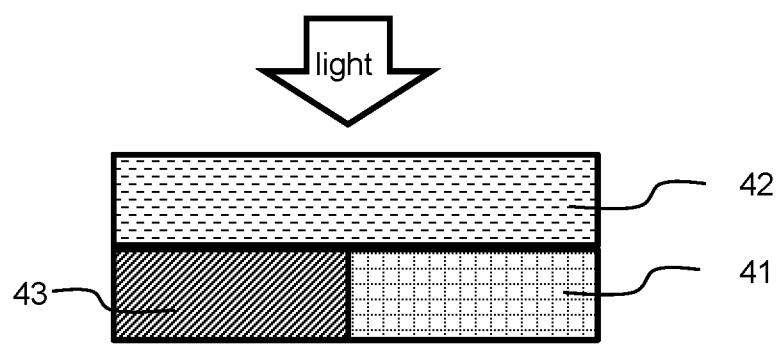

PHOTOELECTRIC CONVERSION ELEMENT AND IMAGE SENSOR USING SAME

TECHNICAL FIELD

The present invention relates to a photoelectric conversion element capable of converting light into electric energy, and to an image sensor using the photoelectric conversion element.

BACKGROUND ART

A photoelectric conversion element capable of converting light into electric energy can be utilized for solar cells, an image sensor, or the like. In particular, an image sensor for reading out the current generated from incident light in a photoelectric conversion element by a CCD or CMOS circuit is widely used.

Conventionally, in an image sensor using a photoelectric conversion element, an inorganic material has been used as a material for forming a photoelectric conversion film. However, since the inorganic material has low color selectivity, it has been required to selectively transmit each of the red, green and blue colors to incident light using a color filter, and to absorb the respective lights by a photoelectric conversion film. However, when a color filter is used, the pitch of an object interferes with the pitch of an image element when a fine object is taken, and an image different from the original image is generated (this is referred to as a moire defect). In order to suppress the defect, an optical lens or the like is required, but there is a disadvantage that the light utilization efficiency and the aperture ratio are lowered by the color filter and the optical lens.

On the other hand, in recent years, there has been an increasing demand for high resolution of an image sensor, and the fineness of the pixels has been advanced. Accordingly, although the size of the pixel becomes smaller, as a result of decreasing the size of the pixel, the amount of the light reaching the photoelectric conversion element of each pixel is decreased, and therefore, reduction in the sensitivity becomes a problem.

In order to solve this problem, researches on the photoelectric conversion element using an organic compound have been made. Since an organic compound can selectively absorb the light in a specific wavelength region out of the incident light by designing the molecular structure, a color filter is not required. Further, the absorption coefficient is high, and therefore, the light utilization efficiency can be increased.

As a photoelectric conversion element using an organic compound, specifically, an element having a constitution in which a pn junction structure or a bulk heterojunction structure is introduced into a photoelectric conversion film sandwiched between both electrodes is known (for example, see PTLs 1 to 3). In addition, in order to decrease dark current, an element having a constitution in which a charge blocking layer is inserted is also known (for example, see PTL 4).

CITATION LISTS

Patent Literatures

[PTL 1] JP 2009-290190 A
[PTL 2] JP 2011-077198 A
[PTL 3] JP 2002-076391 A
[PTL 4] JP 5-129576 A

SUMMARY OF INVENTION

Technical Problem

However, in the photoelectric conversion element using an organic compound, although the superiority has been confirmed in principle particularly for image sensor applications, there are many technical problems for the practical application.

Specifically, in a case where the photoelectric conversion element is formed of two or more kinds of photoelectric conversion materials, the absorption wavelength range is widened, and it becomes a problem that selective absorption of a specific color becomes difficult. Further, it becomes a problem to form a stable film with fewer defects and to reduce the dark current. In addition, it becomes a problem to optimize the transportation balance of holes and electrons and to improve the photoelectric conversion efficiency.

Therefore, an object of the present invention is to provide a photoelectric conversion element, which overcomes these problems of conventional techniques, exhibits high color selectivity, and has low dark current and high photoelectric conversion efficiency.

Solution to Problem

The present invention is a photoelectric conversion element including a first electrode, a second electrode, and at least one organic layer being present between the first electrode and the second electrode, in which the organic layer contains a compound represented by general formula (1), and a compound represented by general formula (2).

[Chem. 1]

(In the formula, A is a group represented by general formula (3);

B is a group selected from the group consisting of an alkoxy group, an alkylthio group, an aryl ether group, an aryl thioether group, an amino group, a furanyl group, a thiophenyl group, a pyrrolyl group, a benzofuranyl group, a benzothiophenyl group, an indolyl group, a dibenzofuranyl group, a dibenzothiophenyl group, and a carbazolyl group;

C is an aromatic heterocyclic group containing an electron-accepting nitrogen, or a group selected from the group consisting of an alkyl group, a cycloalkyl group, an alkenyl group, a cycloalkenyl group, an alkynyl group, an aryl group, and a heteroaryl group, and substituted with a halogen or a cyano group; and each of m and n represents an integer of 1 to 4.

[Chem. 2]

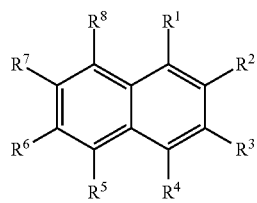

(3)

Herein, $R^1$ to $R^8$ may be the same as or different from one another, and are each a group selected from the group consisting of a hydrogen atom, an alkyl group, a cycloalkyl group, an alkenyl group, a cycloalkenyl group, an alkynyl group, and an aryl group. $R^1$ to $R^8$ may form a monocyclic or condensed ring by bonding adjacent groups among $R^1$ to $R^8$ to each other.

Provided that in general formula (1), B is linked at any m positions of $R^1$ to $R^8$ and a monocyclic or condensed ring formed by bonding any adjacent groups among $R^1$ to $R^8$ to each other, and in general formula (2), C is linked at any n positions of $R^1$ to $R^8$ and a monocyclic or condensed ring formed by bonding any adjacent groups among $R^1$ to $R^8$ to each other.

Further, A in general formula (1) and A in general formula (2) are the same groups.)

Advantageous Effects of Invention

According to the present invention, a photoelectric conversion element that exhibits high color selectivity, and has low dark current and high photoelectric conversion efficiency can be provided.

BRIEF DESCRIPTION OF DRAWINGS

FIG. 1 is a schematic cross-sectional view showing an example of a photoelectric conversion element of the present invention.

FIG. 2 is a schematic cross-sectional view showing an example of a photoelectric conversion element of the present invention.

FIG. 3 is a schematic cross-sectional view showing an example of a photoelectric conversion element of the present invention.

FIG. 4 is a schematic cross-sectional view showing an example of a photoelectric conversion element of the present invention.

FIG. 5 is a schematic view showing a molecular orientation state of a photoelectric conversion layer formed of one kind of compound.

FIG. 6 is a schematic view showing a molecular orientation state of a photoelectric conversion layer in the present invention.

FIG. 7 is a schematic view showing a molecular orientation state of a photoelectric conversion layer formed of two kinds of compounds having different skeletons.

FIG. 8 is a schematic cross-sectional view showing an example of a photoelectric conversion element in which a photoelectric conversion layer has an uneven structure.

FIG. 9 is a schematic cross-sectional view showing an example of a laminated structure of a photoelectric conversion element in an image sensor of the present invention.

FIG. 10 is a schematic cross-sectional view showing an example of a laminated structure of a photoelectric conversion element in an image sensor of the present invention.

DESCRIPTION OF EMBODIMENTS

<Photoelectric Conversion Element>

The photoelectric conversion element of the present invention is a photoelectric conversion element including at least one organic layer being present between a first electrode and a second electrode and converting light into electric energy, in which the organic layer contains a compound represented by general formula (1), and a compound represented by general formula (2).

Both the compound represented by general formula (1) and the compound represented by general formula (2) are preferred in that the light absorption coefficient in a visible region is high. The visible region is a wavelength range of 400 nm to 700 nm.

Examples of the photoelectric conversion element of the present invention are shown in FIGS. 1 to 4. FIG. 1 is an example of a photoelectric conversion element having a first electrode 10, a second electrode 20, and at least one organic layer 15 being interposed between the first electrode and the second electrode. The organic layer includes a photoelectric conversion layer that converts light into electric energy. Hereinafter, the case where the first electrode 10 is a cathode and the second electrode 20 is an anode will be described as an example.

Between the cathode and the anode, a charge blocking layer may be inserted as shown in FIGS. 2 to 4, in addition to the constitution consisting of only one photoelectric conversion layer. The charge blocking layer is a layer having a function of blocking electrons or holes, and functions as an electron blocking layer 13 in a case where the charge blocking layer is inserted between the cathode and the photoelectric conversion layer, and as a hole blocking layer 17 in a case where the charge blocking layer is inserted between the anode and the photoelectric conversion layer. The photoelectric conversion element may include only one of these layers or both of these layers.

In a case where the photoelectric conversion layer is formed of two or more kinds of photoelectric conversion materials, the photoelectric conversion layer may be a monolayer in which two or more kinds of photoelectric conversion materials are mixed, or a multilayer in which layers respectively including one or more kinds of photoelectric conversion materials are laminated. Further, the photoelectric conversion layer may have a constitution in which a mixed layer and each single layer are laminated.

(Compounds Represented by General Formula (1) and General Formula (2))

The compounds represented by general formula (1) and general formula (2) in the present invention will be described in detail.

[Chem. 3]

(1)

(2)

In the formula, A is a group represented by general formula (3);

B is a group selected from the group consisting of an alkoxy group, an alkylthio group, an aryl ether group, an aryl thioether group, an amino group, a furanyl group, a thiophenyl group, a pyrrolyl group, a benzofuranyl group, a benzothiophenyl group, an indolyl group, a dibenzofuranyl group, a dibenzothiophenyl group, and a carbazolyl group;

C is an aromatic heterocyclic group containing an electron-accepting nitrogen, or a group selected from the group consisting of an alkyl group, a cycloalkyl group, an alkenyl group, a cycloalkenyl group, an alkynyl group, an aryl group, and a heteroaryl group, and substituted with a halogen or a cyano group; and each of m and n represents an integer of 1 to 4.

[Chem. 4]

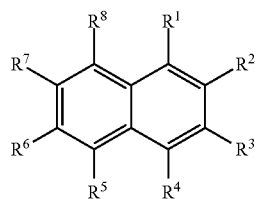

(3)

Herein, $R^1$ to $R^8$ may be the same as or different from one another, and are each a group selected from the group consisting of a hydrogen atom, an alkyl group, a cycloalkyl group, an alkenyl group, a cycloalkenyl group, an alkynyl group, and an aryl group. $R^1$ to $R^8$ may form a monocyclic or condensed ring by bonding adjacent groups among $R^1$ to $R^8$ to each other.

Provided that in general formula (1), B is linked at any m positions of $R^1$ to $R^8$ and a monocyclic or condensed ring formed by bonding any adjacent groups among $R^1$ to $R^8$ to each other, and in general formula (2), C is linked at any n positions of $R^1$ to $R^8$ and a monocyclic or condensed ring formed by bonding any adjacent groups among $R^1$ to $R^8$ to each other.

Further, A in general formula (1) and A in general formula (2) are the same groups.

Among these substituents, hydrogen may be deuterium. In addition, the alkyl group indicates, for example, a saturated aliphatic hydrocarbon group such as a methyl group, an ethyl group, an n-propyl group, an isopropyl group, an n-butyl group, a sec-butyl group, and a tert-butyl group, and may or may not have a substituent. The additional substituent in a case of being substituted is not particularly limited, and examples of the additional substituent include an alkyl group, an aryl group, and a heteroaryl group. This point applies also to the following description. In addition, the number of carbon atoms of the alkyl group is not particularly limited, but is usually in the range of 1 or more to 20 or less and more preferably 1 or more to 8 or less, from the viewpoints of the ease of availability and the cost.

The cycloalkyl group indicates, for example, a saturated alicyclic hydrocarbon group such as cyclopropyl, cyclohexyl, norbornyl, and adamantyl, and may or may not have a substituent. The number of carbon atoms of the alkyl group moiety is not particularly limited, but is usually in the range of 3 or more to 20 or less.

The alkenyl group indicates, for example, an unsaturated aliphatic hydrocarbon group containing a double bond, such as a vinyl group, an allyl group, and a butadienyl group, and may or may not have a substituent. The number of carbon atoms of the alkenyl group is not particularly limited, but is usually in the range of 2 or more to 20 or less.

The cycloalkenyl group indicates, for example, an unsaturated alicyclic hydrocarbon group containing a double bond, such as a cyclopentenyl group, a cyclopentadienyl group, and a cyclohexenyl group, and may or may not have a substituent. The number of carbon atoms of the cycloalkenyl group is not particularly limited, but is usually in the range of 2 or more to 20 or less.

The alkynyl group indicates, for example, an unsaturated aliphatic hydrocarbon group containing a triple bond, such as an ethynyl group, and may or may not have a substituent. The number of carbon atoms of the alkynyl group is not particularly limited, but is usually in the range of 2 or more to 20 or less.

The aryl group indicates, for example, an aromatic hydrocarbon group such as a phenyl group, a naphthyl group, a biphenyl group, a fluorenyl group, a phenanthryl group, a triphenylenyl group, and a terphenyl group, and may or may not have a substituent. The number of carbon atoms of the aryl group is not particularly limited, but is usually in the range of 6 or more to 40 or less.

The alkoxy group indicates, for example, a functional group in which an aliphatic hydrocarbon group is bonded via an ether bond, such as a methoxy group, an ethoxy group, and a propoxy group. The aliphatic hydrocarbon group may or may not have a substituent. The number of carbon atoms of the alkoxy group is not particularly limited, but is usually in the range of 1 or more to 20 or less.

The alkylthio group refers to the one in which the oxygen atom of the ether bond of the alkoxy group is substituted with a sulfur atom. The hydrocarbon group of the alkylthio group may or may not have a substituent. The number of carbon atoms of the alkylthio group is not particularly limited, but is usually in the range of 1 or more to 20 or less.

The aryl ether group indicates, for example, a functional group in which an aromatic hydrocarbon group is bonded via an ether bond, such as a phenoxy group, and the aromatic hydrocarbon group may or may not have a substituent. The number of carbon atoms of the aryl ether group is not particularly limited, but is usually in the range of 6 or more to 40 or less.

The aryl thioether group refers to the one in which the oxygen atom of the ether bond of the aryl ether group is substituted with a sulfur atom. The aromatic hydrocarbon group in the aryl ether group may or may not have a substituent. The number of carbon atoms of the aryl ether group is not particularly limited, but is usually in the range of 6 or more to 40 or less.

The amino group may or may not have a substituent. Examples of the substituent include an aryl group, and a heteroaryl group, and these substituents may further be substituted.

The furanyl group may or may not have a substituent. Examples of the substituent include an alkyl group, an aryl group, and a heteroaryl group, and these substituents may further be substituted.

The thiophenyl group may or may not have a substituent. Examples of the substituent include an alkyl group, an aryl group, and a heteroaryl group, and these substituents may further be substituted.

The pyrrolyl group may or may not have a substituent. Examples of the substituent include an alkyl group, an aryl group, and a heteroaryl group, and these substituents may further be substituted.

The benzofuranyl group may or may not have a substituent. Examples of the substituent include an alkyl group, an aryl group, and a heteroaryl group, and these substituents may further be substituted.

The benzothiophenyl group may or may not have a substituent. Examples of the substituent include an alkyl group, an aryl group, and a heteroaryl group, and these substituents may further be substituted.

The indolyl group may or may not have a substituent. Examples of the substituent include an alkyl group, an aryl group, and a heteroaryl group, and these substituents may further be substituted.

The dibenzofuranyl group may or may not have a substituent. Examples of the substituent include an alkyl group, an aryl group, and a heteroaryl group, and these substituents may further be substituted.

The dibenzothiophenyl group may or may not have a substituent. Examples of the substituent include an alkyl group, an aryl group, and a heteroaryl group, and these substituents may further be substituted.

The carbazolyl group may or may not have a substituent. Examples of the substituent include an alkyl group, an aryl group, and a heteroaryl group, and these substituents may further be substituted.

The heteroaryl group indicates a cyclic aromatic group having one or multiple atoms other than carbon in the ring, such as a furanyl group, a thiophenyl group, a pyridyl group, a quinolinyl group, a pyrazinyl group, a pyrimidinyl group, a triazinyl group, a naphthylidyl group, a benzofuranyl group, a benzothiophenyl group, and an indolyl group, and may or may not be substituted. The number of carbon atoms of the heteroaryl group is not particularly limited, but is usually in the range of 2 or more to 30 or less.

The halogen indicates fluorine, chlorine, bromine, and iodine.

Linking with B or C at any position of $R^1$ to $R^8$ means that B or C directly bonds to the carbon atom at the root where $R^1$ to $R^8$ are bonded in the naphthalene ring of A.

Linking with B or C at any position of a monocyclic or condensed ring formed by bonding any adjacent groups among $R^1$ to $R^8$ to each other means that any one of the carbon atoms constituting the mother skeleton of the monocyclic or condensed ring directly bonds to B or C, and for example, means a case where when $R^2$ and $R^3$ are bonded to each other to form a 6-membered ring, any one or more carbon atoms among the four carbon atoms capable of further bonding with other atoms in the 6-membered ring directly bond to B or C.

The compound represented by general formula (1) has a group represented by B in the molecule. The group represented by B is the groups as described above, and these groups are electron donating groups. The compound represented by general formula (1) has a high hole transporting property by containing B that has an electron donating property in the molecule. Therefore, holes generated in a photoelectric conversion layer can be efficiently transported to the electrode side, and high photoelectric conversion efficiency can be obtained. Further, in the compound represented by general formula (1), by containing B in the molecule, the intermolecular interaction is suppressed, and the width of the absorption spectrum is narrowed. Accordingly, the selectivity of the absorption wavelength is improved. Furthermore, aggregation of molecules can be prevented, and therefore, a compound that is stable with time and has high photoelectric conversion efficiency can be obtained.

B is preferably a group selected from the group consisting of an amino group, a furanyl group, a thiophenyl group, a pyrrolyl group, a benzofuranyl group, a benzothiophenyl group, an indolyl group, a dibenzofuranyl group, a dibenzothiophenyl group, a carbazolyl group, a phenoxy group, a methoxy group, a methylthio group, and a phenylthio group. In this case, by increasing the number of B, the conjugation is further extended, and therefore, the maximum absorption wavelength of the compound represented by general formula (1) can be arbitrarily selected.

Among them, B is more preferably a benzofuranyl group, a benzothiophenyl group, an indolyl group, a dibenzofuranyl group, a phenoxy group, a methoxy group, a methylthio group, and a phenylthio group; furthermore preferably a benzofuranyl group, a benzothiophenyl group, and an indolyl group; and particularly preferably a benzofuranyl group.

In a case where the compound represented by general formula (1) contains multiple Bs, the Bs may be the same as or different from one another.

The compound represented by general formula (2) has a group represented by C in the molecule. The group represented by C is the groups as described above, and these groups are electron accepting groups. The compound represented by general formula (2) has a high electron transporting property by containing C that has an electron accepting property in the molecule. Therefore, electrons generated in a photoelectric conversion layer can be efficiently transported to the electrode side, and high photoelectric conversion efficiency can be obtained. Further, in the compound represented by general formula (2), by containing C in the molecule, the intermolecular interaction is suppressed, and the width of the absorption spectrum is narrowed. Accordingly, the selectivity of the absorption wavelength is improved. Furthermore, aggregation of molecules can be prevented, and therefore, a compound that is stable with time and has high photoelectric conversion efficiency can be obtained.

C is preferably an aromatic heterocyclic group containing an electron-accepting nitrogen, or an alkyl group, an alkenyl group, an aryl group, or a heteroaryl group, and substituted with a halogen or a cyano group. In this case, by increasing the number of C, the conjugation is further extended, and therefore, the maximum absorption wavelength of the compound represented by general formula (2) can be arbitrarily selected.

As the aromatic heterocyclic group containing an electron-accepting nitrogen herein, a pyrimidyl group is preferred. As the aryl group herein, a phenyl group is preferred. As the heteroaryl group herein, a pyrimidyl group is preferred.

Among them, C is preferably an alkenyl group, an aryl group, or a heteroaryl group, substituted with a cyano group, and particularly preferably a group represented by —CH=C(CN)$_2$, a phenyl group substituted with a cyano group, and a pyrimidyl group substituted with a cyano group.

Further, C is similarly preferably an alkyl group or an aryl group, substituted with a halogen, and more preferably substituted with fluorine because of having the highest electron accepting property, and a phenyl group substituted with fluorine is particularly preferred.

In a case where the compound represented by general formula (2) contains multiple Cs, the Cs may be the same as or different from one another.

In addition, the remaining groups from $R^1$ to $R^8$ may be any one selected from among a hydrogen atom, an alkyl group, a cycloalkyl group, an alkenyl group, a cycloalkenyl group, an alkynyl group, and an aryl group. From the viewpoint of the easiness of vacuum vapor deposition, it is preferred that the substituents are appropriately combined so that the molecular weight of the compound represented by general formula (1) and the compound represented by general formula (2) is 300 to 700. Among these groups, hydrogen is preferred because a narrow full width at half maximum can be easily obtained in the absorption spectrum.

In the group represented by general formula (3), $R^1$ to $R^8$ may form a conjugated condensed ring by bonding any adjacent groups among $R^1$ to $R^8$ (for example, $R^1$ and $R^2$ in general formula (3)) to each other. In particular, the skeleton represented by general formula (3) largely contributes to the improvement in charge transportability by the formation of π-electron interaction. Further, when the number of rings of the formed condensed rings becomes three or more rings in total, the effect of improving the charge transportability becomes remarkable. Moreover, when the ring is a condensed ring of three or more rings, the absorption wavelength in the visible region and the high charge transportability can be imparted.

In order to realize the high charge transportability, preferably, A forms a condensed ring consisting of 3 to 6 rings in total; more preferably, A forms a condensed ring consisting of 4 to 6 rings in total; furthermore preferably, A forms a condensed ring consisting of 4 to 5 rings in total; and particularly preferably, A forms a condensed ring consisting of 4 rings in total. By setting the number of rings to these ranges, the molecular weight is optimized for vacuum vapor deposition. In addition, since the conjugation is extended by increasing the number of rings, the absorption spectrum has longer wavelengths, and therefore, the number of rings is adjusted and the absorption wavelength can also be arbitrarily set.

As the constituent element of the condensed ring, carbon is preferred from the viewpoint of being a material capable of transporting holes and electrons. However, in a case of adjusting the energy level or in a case of enhancing the transportability of either holes or electrons, the constituent element is not limited to carbon, and a constitution in which any element selected from nitrogen, oxygen, sulfur, phosphorus, and silicon in addition to carbon is also contained may be taken. Moreover, the condensed ring may be condensed further with another ring.

Preferred examples of the skeleton represented by general formula (3) include ring structures of anthracene, phenanthrene, naphthacene, pyrene, chrysene, triphenylene, fluoranthene, benzofluoranthene, perylene, pentacene, hexacene, and the like, but not limited thereto. In a case of using these skeletons, the linking position of the substituent B or the substituent C may be any position at which as long as the substituent B or the substituent C is linked with a bondable carbon atom, but from the viewpoint of the easiness of synthesis, it is preferred to use positions "a" among the bonding positions of the skeleton shown below.

[Chem. 5]

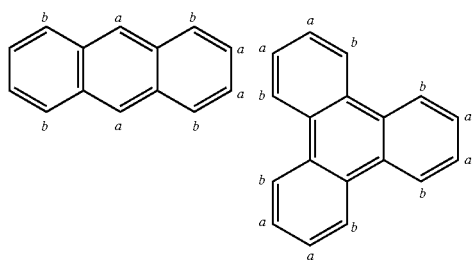

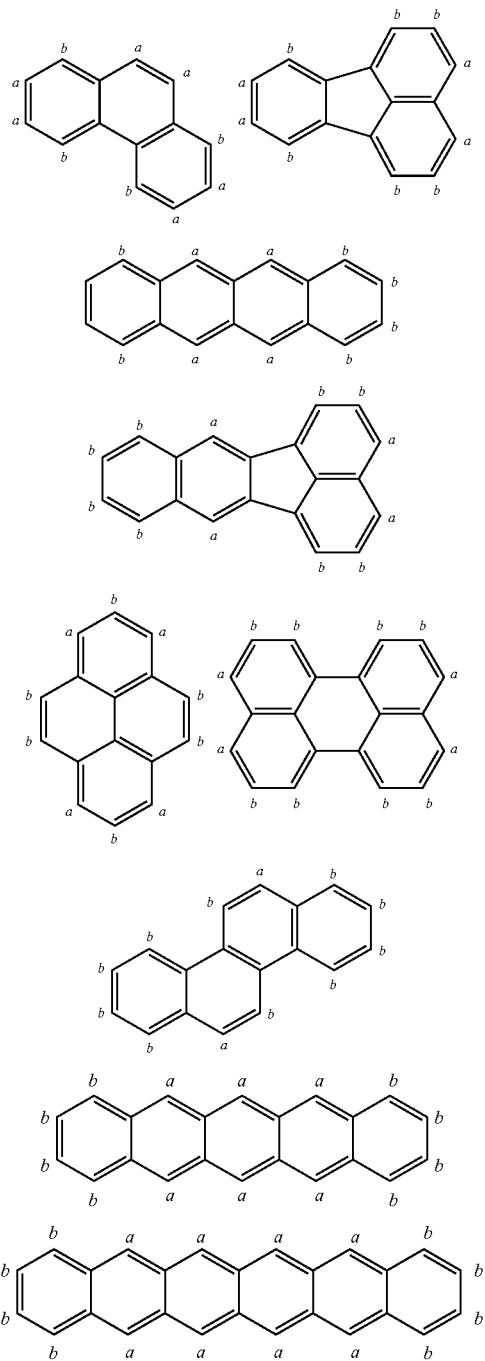

The number of m of substituents B and the number of n of substituents C, which are bonded to the skeleton represented by general formula (3), are not particularly limited, but are usually in the range of 1 or more to 8 or less, respectively. By increasing the numbers of the substituents B and the substituents C, the absorption spectra of the compounds represented by general formula (1) and general formula (2) have longer wavelengths. Accordingly, by adjusting the numbers of the substituents B and the substituents C, the maximum absorption wavelengths of the compounds represented by general formula (1) and general formula (2) can be arbitrarily selected, respectively.

It is preferred that m and n are set so that the absorption spectra of the compounds represented by general formula (1) and general formula (2) are in the same wavelength ranges from the viewpoint of improving the color selectivity, respectively. The same wavelength range is not required to be strictly the same as each other. Specifically, it is preferred that the difference between the maximum values of the absorption spectra of the compound represented by general formula (1) and the compound represented by general formula (2) is 50 nm or less.

As an example, it is preferred to be m=n.

Further, for example, in a case where a benzofuranyl group is used as the substituent B, and a dicyanovinyl group is used as the substituent C, since the dicyanovinyl group is more easily shifted to the longer wavelength than the benzofuranyl group is, it is preferred to be m>n, and more preferred to be m=n+2. As described above, in a case where the shift width of the absorption spectrum is different between the substituent B and the substituent C, it does not necessarily have to be m=n.

More preferably, m is 1 to 3, and furthermore preferably 3. More preferably, n is 1 to 3, and furthermore preferably 1.

In a case where multiple substituents B and substituents C are bonded to the skeleton represented by general formula (3), the kinds of the substituents may be the same as or different from one another, respectively.

Among the skeletons, pyrene, perylene, pentacene and hexacene are preferred because of having favorable charge transport capability, and in particular, pyrene represented by general formula (4) is mentioned as a favorable skeleton from the viewpoint of the easiness of synthesis, the high light absorption coefficient, and the excellent wavelength selectivity.

[Chem. 6]

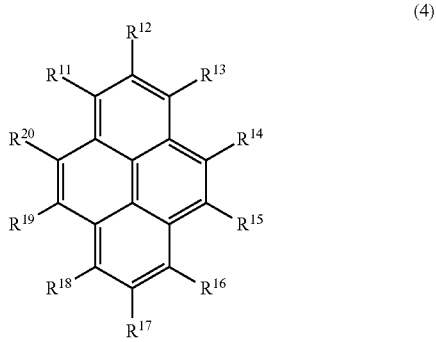

(4)

Herein, $R^{11}$ to $R^{20}$ of general formula (4) may be the same as or different from one another, and are each a group selected from the group consisting of a hydrogen atom, an alkyl group, a cycloalkyl group, an alkenyl group, a cycloalkenyl group, an alkynyl group, and an aryl group. $R^{11}$ to $R^{20}$ may form a monocyclic or condensed ring by bonding adjacent groups among $R^{11}$ to $R^{20}$ to each other. However, in general formula (4), either the substituent B or the substituent C is linked at any position of $R^{11}$ to $R^{20}$ and a condensed ring formed by bonding any adjacent groups among $R^{11}$ to $R^{20}$ to each other.

The substituent B and substituent C may be placed at any position among $R^{11}$ to $R^{20}$ of a pyrene skeleton represented by general formula (4), but are preferred, from the viewpoint of the easiness of synthesis, to be substituted at least at one position among $R^{11}$, $R^{13}$, $R^{16}$ and $R^{18}$, or at least at one position among $R^{12}$ and $R^{17}$, respectively. Further, when the positions of the substituent B and the substituent C are arranged to $R^{11}$, $R^{13}$, $R^{16}$, or $R^{18}$, respectively, the spread of the electron cloud becomes favorable, and therefore, this is more preferred from the viewpoint of improving the charge transportability.

The number of the substituents to be arranged in the pyrene skeleton is arbitrarily set according to the intended absorption wavelength. Since the molecular weight of the compound is set to be 300 to 700 so that the vacuum vapor deposition becomes easy, the number of the substituents is usually 1 or more to 4 or less including the numbers of B and C.

$R^{11}$ to $R^{20}$ are preferably a hydrogen atom or an aryl group among the above-mentioned groups. In particular, the portions that are not the substituent B and the substituent C among $R^{11}$, $R^{13}$, $R^{16}$, and $R^{18}$ (these referred to as "remaining Rs") are preferably a hydrogen atom or an aryl group. Further, it is particularly preferred that the remaining Rs are all hydrogen atoms, respectively.

The compound represented by general formula (1) and the compound represented by general formula (2) may be contained in any layer among the organic layers in a photoelectric conversion element, but it is preferred that the organic layers have a constitution of a multilayer, and in one layer of the organic layers, both of the compound represented by general formula (1) and the compound represented by general formula (2) are contained.

In addition, the layer is preferably a bulk heterojunction layer by the compound represented by general formula (1) and the compound represented by general formula (2). The bulk heterojunction layer will be described later.

Further, in the layer, the mixture ratio of the compound represented by general formula (1) and the compound represented by general formula (2) is preferably 1:3 to 3:1.

As the constitution of the photoelectric conversion layer, a bulk heterojunction layer in which the compound represented by general formula (1) and the compound represented by general formula (2) are mixed in the same layer by a technique such as co-deposition is preferred. By forming the bulk heterojunction layer, the photoelectric conversion layer can form a stable amorphous structure.

Note that the bulk heterojunction layer refers to a structure in which two or more kinds of compounds are randomly mixed in one layer, and the compounds are joined at a nano level with each other. Further, the amorphous means to be non-crystalline and to have a thin film surface with a flat structure. In addition, when the photoelectric conversion layer forms a stable amorphous structure, a current that flows at the time of not irradiating the photoelectric conversion element with light (this is called "dark current") can be reduced in the photoelectric conversion element. When the dark current is reduced, the contrast between a current that flows at the time of light irradiation (this is called "photocurrent") and the dark current is increased, and therefore, a high-performance image element with less noise can be realized.

The reason why the stable amorphous structure is formed by forming the bulk heterojunction layer with the compound represented by general formula (1) and the compound represented by general formula (2) will be described with reference to FIGS. 5 to 8.

FIGS. 5 to 7 are schematic views showing oriented states of compound molecules in a photoelectric conversion film. Further, FIG. 8 is a schematic cross-sectional view of a photoelectric conversion element.

First, in a case of a photoelectric conversion film formed of only the compound 31 represented by general formula (1) as shown in FIG. 5(*a*), or a photoelectric conversion film formed of only the compound 32 represented by general formula (2) as shown in FIG. 5(*b*), a weak attractive force acts between π electrons of the same molecules, and therefore, the structure becomes an aggregation structure in which molecules are regularly arranged. Accordingly, the photoelectric conversion film is easily crystallized. By crystallizing the photoelectric conversion film, the surface of the photoelectric conversion layer has an uneven structure as shown in FIG. 8. That is, when an electric field is applied to the photoelectric conversion film in the photoelectric conversion element, an electric field is easily applied intensively to the portion with a thin film thickness in the uneven structure, and therefore, increase in the dark current is caused.

On the other hand, in a case of a bulk heterojunction layer in which the compound 31 represented by general formula (1) and the compound 32 represented by general formula (2) are randomly mixed as shown in FIG. 6, even if the compound represented by general formula (1) and the compound represented by general formula (2) have the same skeletons, the substituents are different from each other respectively, and therefore, an aggregate structure tends to become difficult to be taken. As a result, the amorphous photoelectric conversion film is formed. When amorphous photoelectric conversion film is formed, the film surface has a flat structure as shown in FIG. 4, and therefore, a uniform electric field is applied to the entire photoelectric conversion film in the photoelectric conversion element, and the dark current can be reduced.

Further, as shown in FIG. 7, in a case of a photoelectric conversion film formed of a compound 33 and a compound 34, which have different skeletons from each other, although part of the photoelectric conversion layer is an amorphous structure, an aggregate structure is easily taken with the compounds having the same skeletons. Therefore, the photoelectric conversion film is easily crystallized, and the surface of the photoelectric conversion layer tends to have an uneven structure similarly to that shown in FIG. 8. Accordingly, when an electric field is applied to the photoelectric conversion film in the photoelectric conversion element, an electric field is easily applied intensively to the portion with a thin film thickness in the uneven structure, and therefore, increase in the dark current is caused.

Therefore, a constitution of the photoelectric conversion layer, in which the compound represented by general formula (1) and the compound represented by general formula (2) having the same skeletons as and different substituents from each other are mixed in combination in the same layer, is the most preferred form.

The mixture ratio of the compound represented by general formula (1) and the compound represented by general formula (2) is, from the viewpoint of the transportation balance of holes and electrons, preferably in the range of (the compound represented by general formula (1)): (the compound represented by general formula (2))=1:3 to 3:1, more preferably in the range of (the compound represented by general formula (1): (the compound represented by general formula (2))=2:3 to 3:2, and furthermore preferably in the range of (the compound represented by general formula (1)): (the compound represented by general formula (2))=1:1, in terms of a molar ratio.

The compound represented by general formula (1) and the compound represented by general formula (2) have condensed polycyclic aromatic skeletons represented by general formula (3) with high charge transportability, and therefore, can efficiently transfer electric charge. The charge mobility of the compound represented by general formula (1) (that is, hole mobility) and the charge mobility of the compound represented by general formula (2) (that is, electron mobility) are preferably $1\times10^{-9}$ cm$^2$/Vs or more, more preferably $1\times10^{-8}$ cm$^2$/Vs or more, and furthermore preferably $1\times10^{-7}$ cm$^2$/Vs or more, respectively.

The compound represented by general formula (1) and the compound represented by general formula (2) have the same skeletons as each other, and therefore, there is no large difference between the hole mobility of the compound represented by general formula (1) and the electron mobility of the compound represented by general formula (2). Accordingly, the transportation balance of the holes and the electrons becomes favorable, as a result of which the photoelectric conversion efficiency is improved.

Note that the charge mobility in the present specification means a mobility measured by a space charge limited current method (SCLC method). As a reference, page 701 of Adv. Funct. Mater, Vol. 16 (2006), and the like can be mentioned.

The film thickness of the organic layer is preferably 20 nm or more to 200 nm or less from the viewpoint of the suppression of current leak and the reduction of power consumption.

In addition, in general, the shape of the absorption spectrum of an organic thin film varies largely depending on the type of the skeleton, and the compound represented by general formula (1) and the compound represented by general formula (2) have the structures of general formula (3) that are the same skeletons in the molecule. Therefore, the shapes of the absorption spectra become substantially similar shapes to each other. Therefore, as in the present invention, in a case of a constitution in which both of the compound represented by general formula (1) and the compound represented by general formula (2) are contained in a photoelectric conversion layer, the shape of the absorption spectrum becomes sharp, and the color selectivity can be improved.

On the other hand, in a case of forming a photoelectric conversion layer by combining the compounds having different types of skeletons from each other, the shapes of the absorption spectra of the compounds are different from each other. Therefore, the shapes of the absorption spectra tend to become broad, but this is suitably used for the application of absorbing light in the entire visible region as in solar cells or the like.

In a case of applying to an image sensor, it is required to selectively absorb each light in a specific wavelength region, such as red light, green light, and blue light. Therefore, it can be said that a constitution of the photoelectric conversion layer, in which the compound represented by general formula (1) and the compound represented by general formula (2) having favorable color selectivity are mixed in the same layer, is the most preferred form.

Herein, it is indicated that the red light has a wavelength range of roughly 580 to 720 nm, the green light has a wavelength range of roughly 480 to 620 nm, and the blue light has a wavelength range of roughly 380 to 520 nm.

In order to obtain the favorable color selectivity as an image sensor, it is preferred that the absorption spectrum of the photoelectric conversion layer containing both of the compound represented by general formula (1) and the compound represented by general formula (2) is in each wavelength region of the red light, green light, and blue light.

That is, in a case of red light, the absorption spectrum of the photoelectric conversion layer is preferably in a wavelength region of roughly 580 to 720 nm. Similarly, the absorption spectrum of the photoelectric conversion layer is preferably in a wavelength region of roughly 480 to 620 nm in a case of green light, and in a wavelength region of roughly 380 to 520 nm in a case of blue light.

Accordingly, the full width at half maximum of the absorption spectrum of the photoelectric conversion layer containing the compound represented by general formula (1) and the compound represented by general formula (2) is preferably 120 nm or less, and more preferably 100 nm or less.

Further, the full widths at half maximum of the absorption spectra of the compound represented by general formula (1) and the compound represented by general formula (2) are, from the viewpoint of achieving both favorable color selectivity and favorable color reproducibility, both preferably 25 nm or more to 100 nm or less, and more preferably 40 nm or more to 100 nm or less.

The difference between the maximum values of the absorption spectra of the compound represented by general formula (1) and the compound represented by general formula (2) is preferably 50 nm or less, and more preferably 40 nm or less. According to this, the peak of the absorption spectrum becomes single, and the color selectivity is improved.

Next, the photoelectric conversion layer constituting a photoelectric conversion element will be described.

(Photoelectric Conversion Layer)

The photoelectric conversion layer is a layer in which photoelectric conversion occurs to generate an electric charge by absorbing incident light. This may be formed of a single photoelectric conversion material, but is preferably formed of a p-type semiconductor material and an n-type semiconductor material. At this time, the p-type semiconductor material and the n-type semiconductor material may be used singly or in multiple, respectively. The photoelectric conversion material in the photoelectric conversion layer absorbs light, and forms excitons, and then electrons and holes are separated by the n-type semiconductor material and the p-type semiconductor material, respectively. As described above, the separated electrons and holes flow to the respective poles through the conduction band and the valence band to generate electrical energy.

The compound represented by general formula (1) and the compound represented by general formula (2) have a high light absorption coefficient and high charge transportability in the visible region, and therefore, are preferably used for a photoelectric conversion layer in particular among the organic layers. In addition, the photoelectric conversion layer is formed of two or more kinds of photoelectric conversion element materials, and the two kinds among them are preferably the compound represented by general formula (1) and the compound represented by general formula (2).

In a case where the photoelectric conversion layer is formed of two kinds of photoelectric conversion materials of a p-type semiconductor material and an n-type semiconductor material, it is preferred that the compound represented by general formula (1) is used as the p-type semiconductor material, and the compound represented by general formula (2) is used as the n-type semiconductor material. This is because the compound represented by general formula (1) contains B having an electron donating property in the molecule, and therefore, has a characteristic of easily transporting the holes rather than the electrons, and the compound represented by general formula (2) contains C having an electron accepting property in the molecule, and therefore, has a characteristic of easily transporting the electrons rather than the holes.

The n-type semiconductor material referred to herein indicates a semiconductor material with an electron transporting property, which has an electron accepting property and a characteristic of easily accepting electrons (large electron affinity). The p-type semiconductor material referred to herein indicates a semiconductor material with a hole transporting property, which has an electron donating property and a characteristic of easily releasing electrons (low ionization potential).

In other words, when the ionization potential and the electron affinity of the compound represented by general formula (1) are expressed as $Ip_1$, and $Ea_1$, respectively, and the ionization potential and the electron affinity of the compound represented by general formula (2) are expressed as $Ip_2$, and $Ea_2$, respectively, it is preferred to be $Ip_1<Ip_2$, and $Ea_1<Ea_2$. By employing this constitution, an excellent function with high efficiency as a photoelectric conversion element can be exerted. This is because before the holes and electrons generated by incident light are annihilated, the holes and electrons flow the p-type semiconductor and the n-type semiconductor, respectively.

Herein, the ionization potential is defined as the energy difference between the occupied orbital with the highest energy among the molecular orbitals of a compound, and the vacuum level, and the value is measured by using ultraviolet photoelectron spectroscopy. Further, the electron affinity is defined as the energy difference between the unoccupied orbital with the lowest energy among the molecular orbitals of a compound, and the vacuum level, and is determined by the difference between the measurement value of the ionization potential and the measurement value of the bandgap.

Note that when the bandgap, and the absorption edge wavelength on the longest wavelength side of the absorption spectrum measured by ultraviolet-visible spectroscopy are expressed as $E(eV)$, and $\lambda(nm)$, respectively, the bandgap is determined by substituting the values in the equation of $E=1240/\lambda$.

The photoelectric conversion element of the present invention is not limited to the constitution in which only the compound represented by general formula (1) and the compound represented by general formula (2) are contained in a photoelectric conversion layer. For example, in order to improve the hole transporting property or to increase the number of generated carriers of the electron blocking layer, the photoelectric conversion element may have a constitution in which both of the compound represented by general formula (1) and the compound represented by general formula (2) are contained in the photoelectric conversion layer, and the compound represented by general formula (1) is contained in the electron blocking layer. Further, in order to improve the electron transporting property of the hole blocking layer or to increase the number of generated carriers of the electron blocking layer, the photoelectric conversion element may have a constitution in which both of the compound represented by general formula (1) and the compound represented by general formula (2) are contained in the photoelectric conversion layer, and the compound represented by general formula (2) is contained in the hole blocking layer. Furthermore, the photoelectric conversion element may have a constitution in which both of the compound represented by general formula (1) and the compound represented by general formula (2) are contained in the electron blocking layer or the hole blocking layer for the purpose of improving the light absorbability of the entire element.

The photoelectric conversion material for constituting the photoelectric conversion layer is preferably formed only of the above-described compound represented by general formula (1) and compound represented by general formula (2), but is not limited thereto. In order to adjust the carrier balance and the light absorption band, or to improve the light absorption efficiency, a material that has been known since before as a photoelectric conversion material may further be contained in the photoelectric conversion layer.

For example, the p-type semiconductor material may be any organic compound as long as being a hole transporting compound that has a relatively small ionization potential and has an electron donating property. Examples of the p-type organic semiconductor material include a compound having a condensed polycyclic aromatic derivative such as naphthalene, anthracene, phenanthrene, pyrene, chrysene, naphthacene, triphenylene, perylene, fluoranthene, fluorene, and indene, and a derivative thereof; a cyclopentadiene derivative, a furan derivative, a thiophene derivative, a pyrrole derivative, a benzofuran derivative, a benzothiophene derivative, an indole derivative, a pyrazoline derivative, a dibenzofuran derivative, a dibenzothiophene derivative, a carbazole derivative, an indolocarbazole derivative, an aromatic amine derivative such as N,N'-dinaphthyl-N,N'-diphenyl-4,4'-diphenyl-1,1'-diamine, a styrylamine derivative, a benzidine derivative, a porphyrin derivative, a phthalocyanine derivative, and a quinacridone derivative. In particular, a compound having a condensed polycyclic aromatic derivative, and a quinacridone derivative are preferred materials because of being excellent in the hole transporting property.

Examples of the polymer-based p-type organic semiconductor material include a polyphenylene vinylene derivative, a polyparaphenylene derivative, a polyfluorene derivative, a polyvinyl carbazole derivative, and a polythiophene derivative, but not limited particularly thereto.

As the preferred p-type semiconductor material, the above-described materials can be used, but the preferred p-type semiconductor material is not particularly limited thereto.

The n-type semiconductor material may be any material as long as the material is a compound having a high electron affinity and an electron transporting property. Examples of the n-type semiconductor material include a condensed polycyclic aromatic derivative such as naphthalene, and anthracene; a styryl-based aromatic ring derivative typified by 4,4'-bis(diphenylethenyl)biphenyl, a tetraphenyl butadiene derivative, a coumarin derivative, an oxadiazole derivative, a pyrrolopyridine derivative, a perinone derivative, a pyrrolopyrrole derivative, a thiadiazolopyridine derivative, an aromatic acetylene derivative, an aldazine derivative, a pyrromethene derivative, a diketopyrrolo[3,4-c]pyrrole derivative, an azole derivative such as imidazole, triazole, thiadiazole, oxazole, oxadiazole, and triazole and a metal complex thereof, a quinone derivative such as anthraquinone, and diphenoquinone, a phosphorus oxide derivative, a quinolinol complex such as tris(8-quinolinolate)aluminum (III), and various metal complexes such as a benzoquinolinol complex, a hydroxyazole complex, an azomethine complex, a tropolone-metal complex, and a flavonol-metal complex.

Examples of the n-type semiconductor material also include an organic compound having a nitro group, a cyano group, a halogen, or a trifluoromethyl group in the molecule, a quinone-based compound, an acid anhydride-based compound such as a maleic anhydride, and a phthalic anhydride, and fullerene and a fullerene derivative, such as C60 and PCBM.

Further, a compound having a heteroaryl ring structure containing an electron-accepting nitrogen, which is constituted of elements selected from among carbon, hydrogen, nitrogen, oxygen, silicon, and phosphorus, can also be mentioned. The electron-accepting nitrogen referred to herein indicates a nitrogen atom forming a multiple bond with the adjacent atoms. Since a nitrogen atom has a high electronegativity, the multiple bond has an electron-accepting characteristic. Therefore, the aromatic heterocyclic group containing an electron-accepting nitrogen has a high electron affinity, and is preferred as an n-type semiconductor material.

Examples of the heteroaryl ring containing an electron-accepting nitrogen include a pyridine ring, a pyrazine ring, a pyrimidine ring, a quinoline ring, a quinoxaline ring, a naphthylidine ring, a pyrimidopyrimidine ring, a benzoquinoline ring, a phenanthroline ring, an imidazole ring, an oxazole ring, an oxadiazole ring, a triazole ring, a triazole ring, a thiadiazole ring, a benzo-oxazole ring, a benzothiazole ring, a benzimidazole ring, and a phenanthroimidazole ring.

Examples of the compound having the heteroaryl ring structure include a benzimidazole derivative, a benzoxazole derivative, a benzthiazole derivative, an oxadiazole derivative, a thiadiazole derivative, a triazole derivative, a pyrazine derivative, a phenanthroline derivative, a quinoxaline derivative, a quinoline derivative, a benzoquinoline derivative, an oligopyridine derivative such as bipyridine, and terpyridine, a quinoxaline derivative, and a naphthylidine derivative, as the preferred compound. Among them, an imidazole derivative such as tris(N-phenylbenzimidazole-2-yl) benzene, an oxadiazole derivative such as 1,3-bis[(4-tert-butylphenyl)1,3,4-oxadiazolyl]phenylene, a triazole derivative such as N-naphthyl-2,5-diphenyl-1,3,4-triazole, a phenanthroline derivative such as bathocuproine, and 1,3-bis(1,10-phenanthroline-9-yl)benzene, a benzoquinoline derivative such as 2,2'-bis(benzo[h]quinoline-2-yl)-9,9'-spirobifluorene, a bipyridine derivative such as 2,5-bis(6'-(2', 2"-bipyridyl))-1,1-dimethyl-3,4-diphenylsilole, a terpyridine derivative such as 1,3-bis(4'-(2,2':6'2"-terpyridinyl)) benzene, and a naphthylidine derivative such as bis(1-naphtyl)-4-(1,8-naphthylidine-2-yl)phenylphosphine oxide, are preferably used from the viewpoint of the electron transport capability.

As the preferred n-type semiconductor material, the above-described materials can be used, but the n-type semiconductor material is not particularly limited thereto.

Next, electrodes and a charge blocking layer, which constitute a photoelectric conversion element, will be described.

(Anode and Cathode)

In the photoelectric conversion element of the present invention, the anode and the cathode have a role to allow the electrons and holes produced in the element to flow so as to supply a current sufficiently. In order to make light incident on a photoelectric conversion layer, at least one of the anode and the cathode is desirably transparent or translucent. Usually, it is preferred that a transparent electrode is used as the cathode to be formed on the substrate.

As the cathode, any material can be used as long as being capable of efficiently extracting the holes from the photoelectric conversion layer and being transparent. As the material, a conductive metal oxide such as tin oxide, indium oxide, and indium tin oxide (ITO), a metal such as gold, silver, and chromium, an inorganic conductive substance such as copper iodide, and copper sulfide, a conductive polymer such as polythiophene, polypyrrole, and polyaniline, and the like are preferred, and an ITO glass or a Nesa glass is particularly preferably used.

The resistance of the transparent electrode is favorable as long as being the degree at which the current produced in the element is allowed to flow sufficiently, and is preferably low resistance from the viewpoint of the photoelectric conversion efficiency of the element. For example, an ITO substrate having a resistance of 300 Ω/□ or less functions as an element electrode, and therefore, it is particularly preferred to use a low resistance product.

The thickness of the ITO can be arbitrarily selected according to the resistance value, and the ITO is usually used in the thickness range of 50 to 300 nm in many cases. As the method for forming an ITO film, an electron beam method, a sputtering method, a chemical reaction method, or the like is employed, but the method is not particularly limited.

As the glass substrate, soda-lime glass, alkali-free glass, or the like is used, and as the thickness of the glass substrate, 0.5 mm or more is sufficient as long as being sufficient for maintaining the mechanical strength. As the material of the glass substrate, the less the ions eluted from the glass, the better, and therefore, alkali-free glass is preferred, and soda-lime glass to which barrier coat of $SiO_2$ or the like has been applied can also be used. Moreover, when the cathode stably functions, the substrate is not required to be glass, and for example, the anode may be formed on a plastic substrate.

As the anode, a substance capable of efficiently extracting electrons from the photoelectric conversion layer is preferably used, and examples of the substance include platinum, gold, silver, copper, iron, tin, zinc, aluminum, indium, chromium, lithium, sodium, potassium, calcium, magnesium, cesium, and strontium. In order to improve the element characteristics by enhancing the electron extraction efficiency, a low work-function metal such as lithium, sodium, potassium, calcium, magnesium, and cesium, or an alloy containing these low work-function metals is effective.

A method in which the one obtained by doping a compound to be used as the hole blocking layer described later with a minute amount of lithium, magnesium, or cesium (1 nm or less displayed by a film thickness meter of vacuum vapor deposition) is used as a cathode having high stability can also be mentioned as a preferred example.

Further, an inorganic salt such as lithium fluoride can also be used.

Further, in order to protect electrodes, it is preferred to laminate a metal such as platinum, gold, silver, copper, iron, tin, aluminum, or indium, or an alloy using thereof, an inorganic substance such as silica, titania, and silicon nitride, polyvinyl alcohol, vinyl chloride, a hydrocarbon-based polymer, or the like.

As the method for preparing electrodes, a resistance heating method, an electron beam method, a sputtering method, an ion plating method, a coating method, or the like is preferably employed.

In addition, in a case of using as an image sensor, it is preferred to apply an electric field from the outside so that the cathode becomes a negative potential to the anode. Electrons and holes generated in the photoelectric conversion layer tend to be introduced to the anode side and the cathode side, respectively, and the effect of improving the photoelectric conversion efficiency is exerted. Therefore, it is preferred that the photoelectric conversion element is provided with a voltage application part for applying a voltage to the organic layer.

In this case, the applied voltage is preferably $10^5$ V/m or more to $10^9$ V/m or less from the viewpoint of improving the photoelectric conversion efficiency and of suppressing the current leak.

Further, even if an electric field is not applied between the anode and the cathode, electric charge flows to the photoelectric conversion element by a built-in electric field when the anode and the cathode are connected to a closed circuit, and therefore, the photoelectric conversion element of the present invention can also be used as a photovoltaic element.

(Charge Blocking Layer)

The charge blocking layer is a layer used for taking the electrons and holes, which are photoelectrically converted by the photoelectric conversion layer, from the electrodes efficiently and stability, and examples of the charge blocking layer include an electron blocking layer for blocking electrons and a hole blocking layer for blocking holes. These layers may be formed of an inorganic substance or an organic compound. Further, the layer may also be constituted of a mixed layer of an inorganic substance and an organic compound.

The hole blocking layer is a layer for blocking the recombination of holes and electrons produced in the photoelectric conversion layer when the holes flow to the anode side. According to the type of the material for constituting each layer, the recombination of holes and electrons is suppressed by inserting this layer, and the photoelectric conversion efficiency is improved. Therefore, it is favorable that the HOMO level of the hole blocking material is energetically lower than that of the photoelectric conversion material.

As the hole blocking material, a compound capable of efficiently blocking the movement of holes from the photoelectric conversion layer is preferred. Specific examples of the compound include a quinolinol derivative metal complex typified by 8-hydroxyquinoline aluminum, a tropolone-metal complex, a flavonol-metal complex, a perylene derivative, a perinone derivative, a naphthalene derivative, a coumarin derivative, an oxadiazole derivative, an aldazine derivative, a bisstyryl derivative, a pyrazine derivative, an oligopyridine derivative such as bipyridine, and terpyridine, a phenanthroline derivative, a quinoline derivative, and an aromatic phosphorus oxide compound. These hole blocking materials may be used alone, or in lamination or mixture with other hole blocking materials.

The electron blocking layer is a layer for blocking the recombination of electrons and holes produced in the photoelectric conversion layer when the electrons flow to the cathode side. According to the type of the material for constituting each layer, the recombination of holes and electrons is suppressed by inserting this layer, and the photoelectric conversion efficiency is improved. Therefore, it is favorable that the LUMO level of the electron blocking material is energetically higher than that of the photoelectric conversion material.

As the electron blocking material, a compound capable of efficiently blocking the movement of electrons from the photoelectric conversion layer is preferred. Specific examples of the compound include triphenylamines such as N,N'-diphenyl-N,N'-bis(3-methylphenyl)-4,4'-diphenyl-1,1'-diamine, and N,N'-bis(1-naphthyl)-N,N'-diphenyl-4,4'-diphenyl-1,1'-diamine, bis(N-allylcarbazole) or bis(N-alkylcarbazole)s, a pyrazoline derivative, a stilbene-based compound, a distyryl derivative, a hydrazone-based compound, a heterocyclic compound typified by an oxadiazole derivative, a phthalocyanine derivative, and a porphyrin derivative. Examples of the polymer-based compound include polycarbonate and a styrene derivative, which contain the monomer in the side chain, polyvinyl carbazole, polysilane, and PEDOT/PSS. A compound that forms a thin film required for the production of the element, can extract holes from the photoelectric conversion layer, and further can transport the holes is favorable. These electron blocking materials may be used alone, or in lamination or mixture with other electron blocking materials.

The hole blocking layer and electron blocking layer described above can be used alone or in lamination or mixture of two or more kinds of the materials, or can be used as a polymer binder in a state of being dispersed in a solvent-soluble resin such as polyvinyl chloride, polycarbonate, polystyrene, poly(N-vinyl carbazole), polymethyl methacrylate, polybutyl methacrylate, polyester, polysulfone, polyphenylene oxide, polybutadiene, a hydrocarbon resin, a ketone resin, a phenoxy resin, polysulfone, polyamide, ethyl cellulose, vinyl acetate, an ABS resin, and a polyurethane resin; a curable resin such as a phenol resin, a xylene resin, a petroleum resin, a urea resin, a melamine resin, an unsaturated polyester resin, an alkyd resin, an epoxy resin, and a silicone resin; or the like.

As the method for forming an organic layer, there are a resistance heating vapor deposition method, an electron beam deposition method, a sputtering method, a molecular lamination method, a coating method, and the like, but the method is not particularly limited thereto. Usually, a resistance heating vapor deposition method, or an electron beam deposition method is preferred in terms of characteristics.

<Image Sensor>

The photoelectric conversion element of the present invention can be suitably utilized for an image sensor. The image sensor is a semiconductor element for converting an optical image into electrical signals. In general, an image sensor is constituted of the above-mentioned photoelectric conversion element for converting light into electric energy, and of a circuit for reading out the electric energy in a form of electrical signals. According to the application of the image sensor, multiple photoelectric conversion elements can be arranged on a one-dimensional straight line or a two-dimensional plane.

In a case of a monochrome image sensor, the monochrome image sensor may be constituted of one kind of photoelectric conversion element. Ina case of a color image sensor, the color image sensor is constituted of two or more kinds of photoelectric conversion elements, and for example, is constituted of a photoelectric conversion element for detecting red light, a photoelectric conversion element for detecting green light, and a photoelectric conversion element for detecting blue light. The photoelectric conversion element of each color has a laminated structure, that is, may be laminated on one pixel, or may constitute a matrix structure in which multiple photoelectric conversion elements are arranged side by side.

Further, in a case of a structure in which photoelectric conversion elements are laminated on one pixel, as shown in FIG. 9, the structure may be a three-layer structure in which a photoelectric conversion element for detecting green light 42, a photoelectric conversion element for detecting blue light 43, and a photoelectric conversion element for detecting red light 41 are sequentially laminated, or as shown in FIG. 10, the structure may be a two-layer structure in which a photoelectric conversion element for detecting green light 42 is arranged on the entire surface as an upper layer, and a photoelectric conversion element for detecting red light 41 and a photoelectric conversion element for detecting blue light 43 are formed as the lower layer having a matrix structure. In these structures, the photoelectric conversion element for detecting green light is arranged on a layer nearest to incident light.

The order of the lamination of each color is not limited to the above order, and may be different from the order in FIG. 9. From the viewpoint that the photoelectric conversion element of the uppermost layer absorbs specific color and has a function as a color filter to transmit long wavelength light and short wavelength light other than the specific color, it is preferred to have a constitution in which the photoelectric conversion element for detecting green light is arranged as the uppermost layer. Further, from the viewpoint of the easiness of the detection of short wavelengths, a constitution in which the photoelectric conversion element for detecting blue light is arranged as the uppermost layer may be employed.

In addition, in a case of a matrix structure, the array can be selected from an array such as a Bayer array, a honeycomb array, a striped array, and a delta array. Moreover, for the photoelectric conversion element for detecting green light, an organic photoelectric conversion material is used, and for the photoelectric conversion element for detecting red light and the photoelectric conversion element for detecting blue light, an inorganic photoelectric conversion material that has been conventionally used, and an organic photoelectric conversion material may be used in appropriate combination.

The image sensor of the present invention is constituted of two or more kinds of photoelectric conversion elements, and at least one kind of the photoelectric conversion elements is preferably the photoelectric conversion element described above. Further, the two or more kinds of photoelectric conversion elements preferably have a laminated structure. In particular, a photoelectric conversion layer constituted of the compound represented by general formula (1) and the compound represented by general formula (2) is excellent in the ability to selectively detect a specific wavelength region. Accordingly, the image sensor of the present invention is constituted of photoelectric conversion elements for detecting red light, green light, and blue light, and at least one kind of the photoelectric conversion elements having the above-described laminated structure is preferably a photoelectric conversion element to detect light of these colors.

EXAMPLES

Hereinafter, the present invention will be explained by way of Examples, but should not be limited at all by these examples. Note that the ionization potential of the compounds to be used in Examples and Comparative Examples was measured by using AC-2 (manufactured by RIKEN KEIKI Co., Ltd.). Further, the electron affinity was calculated by using the absorption spectrum measured by using a U-3200 type spectrophotometer (manufactured by Hitachi, Ltd.).

Example 1

A photoelectric conversion element using a compound D-1 and a compound A-1, both having the same skeletons, was prepared as follows.

A glass substrate (manufactured by ASAHI GLASS CO., LTD., 15 Ω/□, electron beam deposited product) on which an ITO transparent conductive film had been deposited to a thickness of 150 nm was cut into a size of 30×40 mm, and etching was performed to the cut substrate. The obtained substrate was subjected to ultrasonic cleaning for 15 minutes using acetone, and "Semico Clean (registered trademark) 56" (manufactured by Furuuchi Chemical Corporation), respectively, and then washed with ultrapure water. Subsequently, the washed substrate was subjected to ultrasonic cleaning for 15 minutes using isopropyl alcohol, then immersed in hot methanol for 15 minutes, and dried. The substrate was subjected to a UV-ozone treatment for one hour immediately before the preparation of the element.

Next, by a spin coating method, PEDOT/PSS (Clevios™ P VP AI4083) was applied to a thickness of 30 nm to the obtained substrate as an electron blocking layer. The substrate was arranged in a vacuum vapor deposition apparatus, and co-deposited to a thickness of 70 nm with a compound D-1 being a p-type semiconductor material and a compound A-1 being an n-type semiconductor material as a photoelectric conversion layer at a vapor-deposition speed ratio of 1:1 after the inside of the apparatus was evacuated until the degree of vacuum became $5 \times 10^{-5}$ Pa or less. Next, to the resultant substrate, aluminum was deposited to a thickness of 60 nm as an anode, and a photoelectric conversion element having a 2×2 mm square was prepared. The film thickness referred to herein is a displayed value of a crystal oscillation type thickness monitor.

Further, in order to prepare a substrate for absorption spectrum measurement, a quartz substrate was placed in the same chamber at the same time as the deposition of the photoelectric conversion layer, and a thin film having a thickness of 70 nm was prepared.

When the absorption spectrum from 400 nm to 700 nm of the deposited film on the quartz substrate was measured, the following light absorption characteristics were obtained. Note that the absorption coefficient was calculated by Lambert-Beer Law.

Maximum absorption wavelength: 471 nm

Full width at half maximum at the maximum absorption wavelength: 98 nm

Absorption coefficient at the maximum absorption wavelength: $6.41 \times 10^4$/cm When a bias voltage (−3 V) was applied to the photoelectric conversion element, the spectral sensitivity characteristics, the photocurrent value, and the dark current value were as follows. Note that the ON/OFF ratio referred to herein means (photocurrent value at the maximum sensitivity wavelength)/(dark current value).

Maximum sensitivity wavelength: 460 nm

External quantum efficiency at the maximum sensitivity wavelength: 40%

Photocurrent value at the maximum sensitivity wavelength: $5.0 \times 10^{-4}$ A/cm$^2$ Dark current value: $4.9 \times 10^{-6}$ A/cm$^2$ ON/OFF ratio: 101

[Chem. 7]

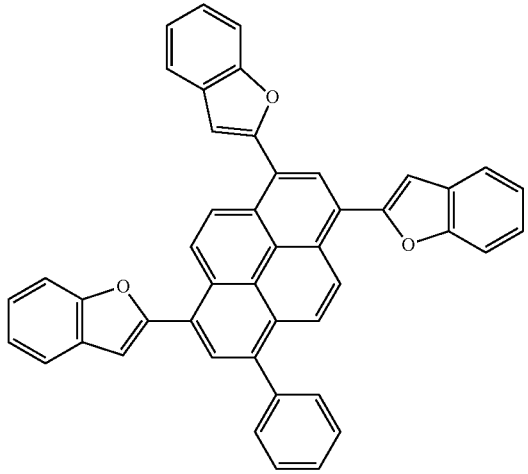

D-1

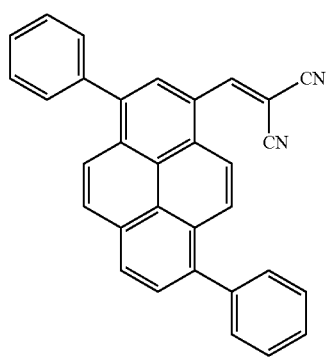

A-1

Examples 2 to 11

The photoelectric conversion element was prepared in the similar manner as in Example 1, except that a p-type semiconductor material and an n-type semiconductor material were deposited in the combination shown in Table 1 in place of the compound D-1 and the compound A-1, when depositing the photoelectric conversion layer. The results are shown in Tables 1 and 2.

[Chem. 8]

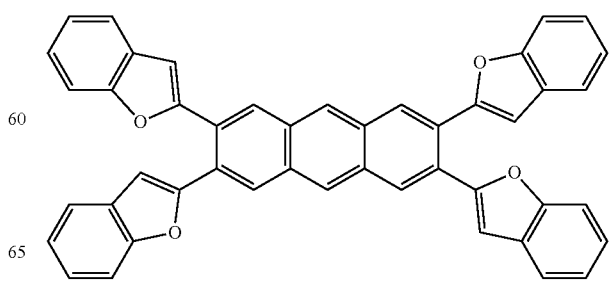

D-2

-continued
A-2
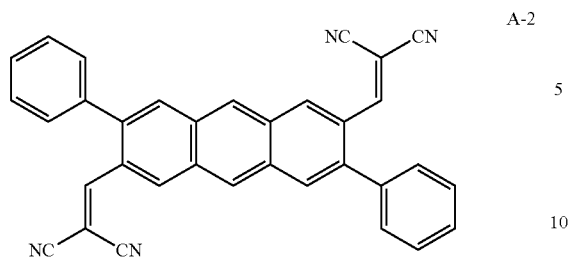
[Chem. 9]
D-3
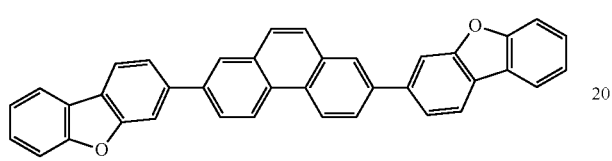
A-3
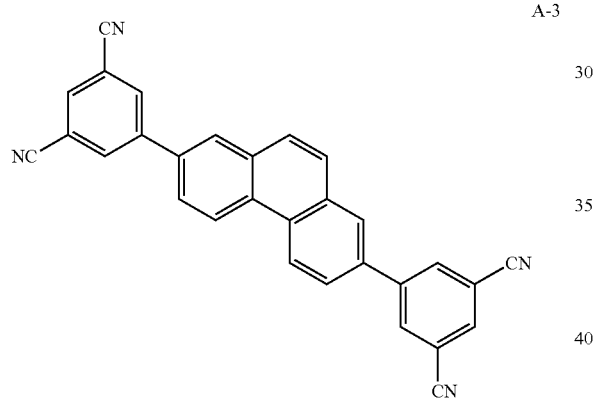
D-4
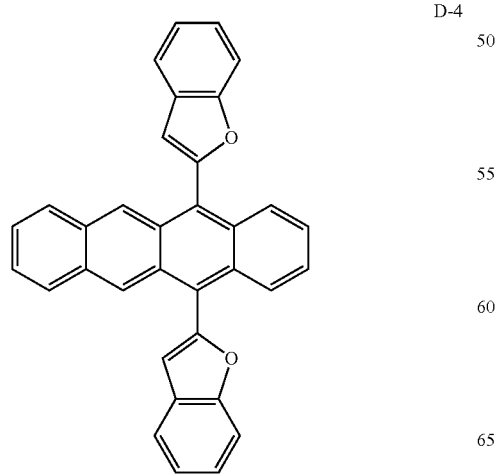
-continued
A-4
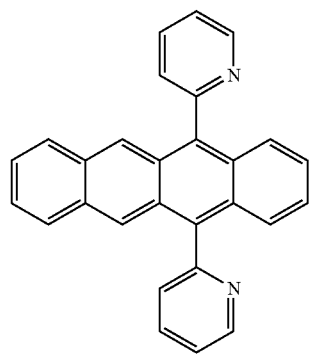
D-5
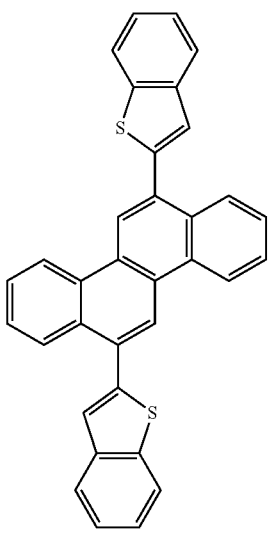
A-5
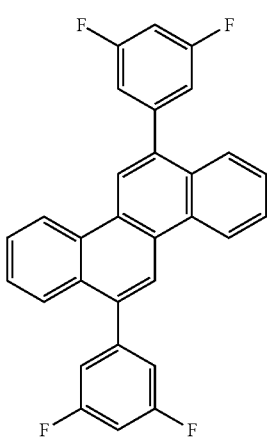

-continued
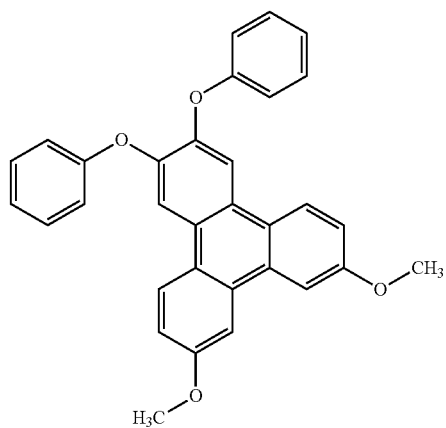
D-6
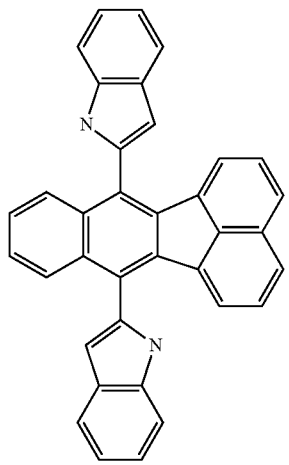
D-8
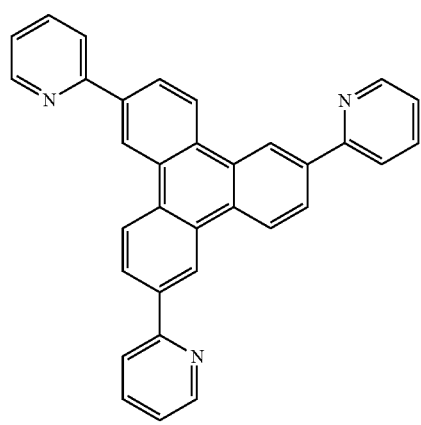
A-6
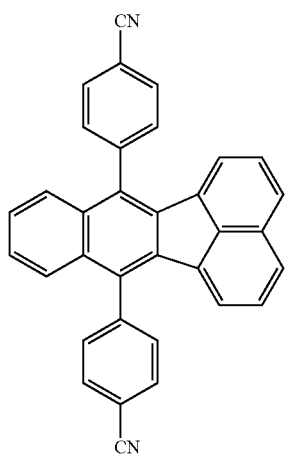
A-8
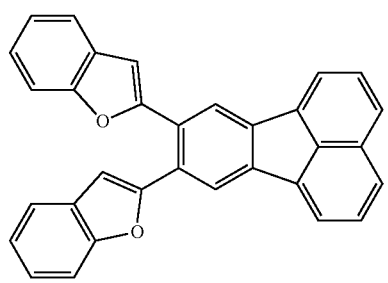
D-7
[Chem. 11]
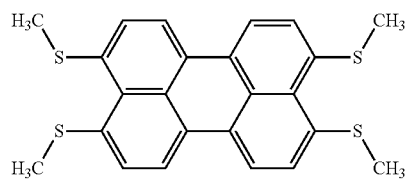
D-9
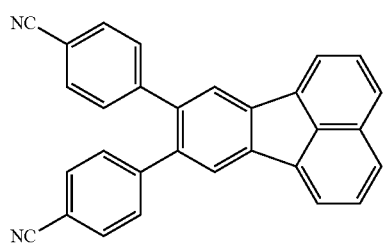
A-7
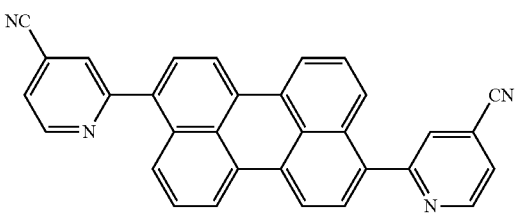
A-9

D-10
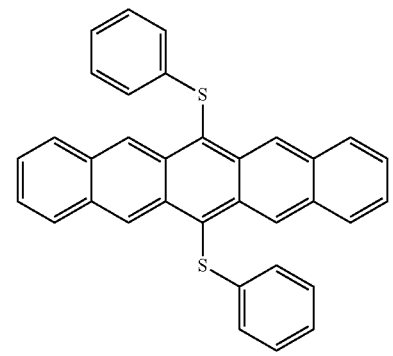

A-10
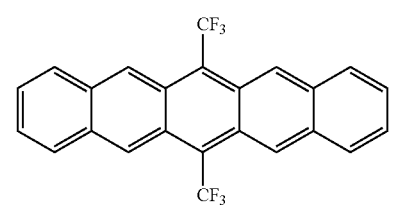

D-11
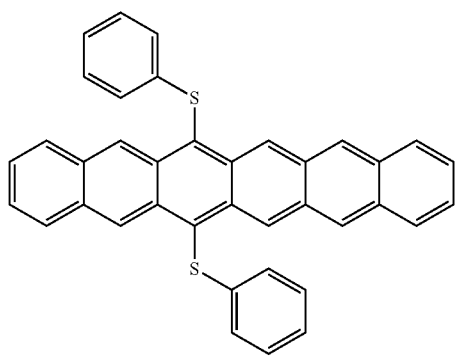

A-11
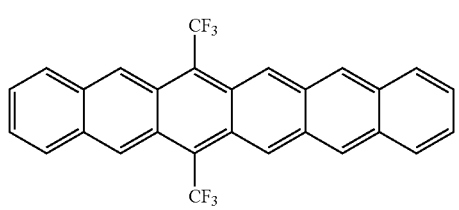

[Chem. 12]

D-12
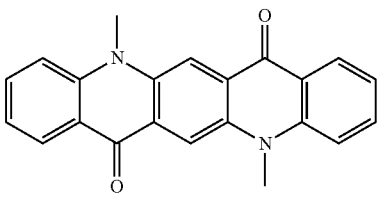

D-13
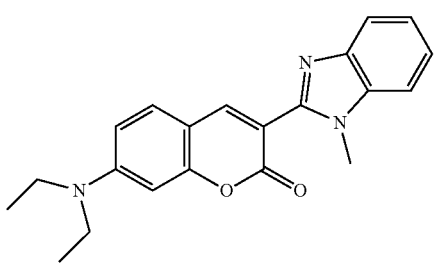

D-14
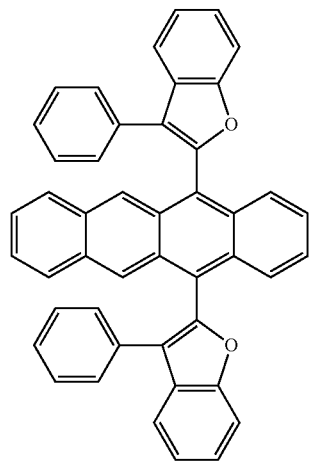

Comparative Examples 1 to 3

The photoelectric conversion element was prepared in the similar manner as in Example 1, except that any one of the compounds D-12, D-13, and D-14 having a different skeleton from that of the compound A-1 was used for the deposition in place of the compound D-1, when depositing the photoelectric conversion layer. The results are shown in Tables 1 and 2. The full width at half maximum at the maximum absorption wavelength became larger as compared with that in Example 1, and therefore, the element having poor color selectivity was obtained. In addition, the balance of the hole transporting property and the electron transporting property was lost, and the external quantum efficiency at the maximum sensitivity wavelength was lowered as compared with that in Example 1. Further, the dark current value became larger as compared with that in Example 1, and therefore, the ON/OFF ratio was lowered.

Comparative Example 4

The photoelectric conversion element was prepared in the similar manner as in Example 1, except that the compound A-15 having a different skeleton from that of the compound D-1 was used for the deposition in place of the compound A-1, when depositing the photoelectric conversion layer. The results are shown in Tables 1 and 2. Although the external quantum efficiency at the maximum sensitivity wavelength was improved, the full width at half maximum at the maximum absorption wavelength became larger as compared with that in Examples, and therefore, the element having poor color selectivity was obtained. Further, the ON/OFF ratio was lowered as compared with that in Example 1.

[Chem. 13]

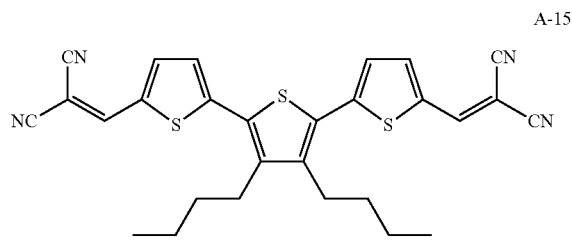

A-15

Comparative Example 5

The photoelectric conversion element was prepared in the similar manner as in Example 1, except that the compound A-16 having a different skeleton from that of the compound A-1 was used for the deposition in place of the compound D-1, when depositing the photoelectric conversion layer. The results are shown in Tables 1 and 2. The full width at half maximum at the maximum absorption wavelength became larger as compared with that in Example 1, and therefore, the element having poor color selectivity was obtained. In addition, the balance of the hole transporting property and the electron transporting property was lost, and the external quantum efficiency at the maximum sensitivity wavelength was lowered as compared with that in Example 1. Further, the dark current value became larger as compared with that in Example 1, and therefore, the ON/OFF ratio was lowered.

[Chem. 14]

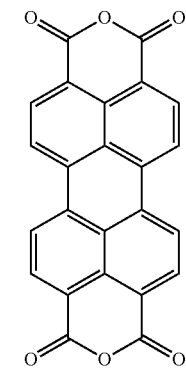

A-16

Comparative Examples 6 and 7

The photoelectric conversion element was prepared in the similar manner as in Example 1, except that only either one of the compound D-1 or the compound A-1 was used for the deposition when depositing the photoelectric conversion layer. The results are shown in Tables 1 and 2. The external quantum efficiency at the maximum sensitivity wavelength was lowered as compared with that in Example 1. Further, the dark current value became larger as compared with that in Example 1, and therefore, the ON/OFF ratio was lowered.

TABLE 1

| | p-Type semiconductor material | | | | | | n-Type semiconductor material | | | | |
|---|---|---|---|---|---|---|---|---|---|---|---|
| | Kind | Maximum absorption wavelength (nm) | Full width at half maximum (nm) | Hole mobility (cm$^2$/vs) | Ionization potential (eV) | Electron affinity (eV) | Kind | Maximum absorption wavelength (nm) | Full width at half maximum (nm) | Electron mobility (cm$^2$/vs) | Ionization potential (eV) | Electron affinity (eV) |
| Example 1 | D-1 | 453 | 99 | $8.5 \times 10^{-6}$ | 5.5 | 3.2 | A-1 | 489 | 100 | $1.5 \times 10^{-6}$ | 6.0 | 3.8 |
| Example 2 | D-2 | 446 | 83 | $4.7 \times 10^{-7}$ | 5.5 | 3.3 | A-2 | 460 | 89 | $1.6 \times 10^{-7}$ | 6.0 | 3.7 |
| Example 3 | D-3 | 421 | 50 | $4.9 \times 10^{-6}$ | 5.7 | 2.9 | A-3 | 404 | 42 | $4.3 \times 10^{-6}$ | 6.4 | 3.5 |
| Example 4 | D-4 | 524 | 98 | $1.4 \times 10^{-7}$ | 5.6 | 3.3 | A-4 | 503 | 84 | $3.8 \times 10^{-7}$ | 6.0 | 3.7 |
| Example 5 | D-5 | 422 | 44 | $3.3 \times 10^{-7}$ | 5.5 | 2.7 | A-5 | 420 | 47 | $8.2 \times 10^{-7}$ | 5.9 | 3.2 |
| Example 6 | D-6 | 550 | 54 | $6.1 \times 10^{-6}$ | 5.4 | 3.3 | A-6 | 539 | 51 | $3.1 \times 10^{-6}$ | 5.9 | 3.7 |
| Example 7 | D-7 | 462 | 69 | $3.8 \times 10^{-6}$ | 5.7 | 3.2 | A-7 | 488 | 59 | $8.9 \times 10^{-7}$ | 6.3 | 3.8 |
| Example 8 | D-8 | 470 | 70 | $2.4 \times 10^{-6}$ | 5.8 | 3.2 | A-8 | 457 | 75 | $1.4 \times 10^{-6}$ | 6.4 | 3.8 |
| Example 9 | D-9 | 522 | 97 | $2.2 \times 10^{-4}$ | 5.5 | 3.3 | A-9 | 513 | 96 | $3.6 \times 10^{-4}$ | 6.2 | 4.1 |
| Example 10 | D-10 | 456 | 94 | $9.3 \times 10^{-3}$ | 5.5 | 3.3 | A-10 | 444 | 83 | $5.6 \times 10^{-3}$ | 6.0 | 3.8 |
| Example 11 | D-11 | 501 | 96 | $8.6 \times 10^{-4}$ | 5.5 | 3.3 | A-11 | 465 | 87 | $4.9 \times 10^{-4}$ | 6.0 | 3.8 |
| Comparative Example 1 | D-12 | 538 | 71 | $2.5 \times 10^{-9}$ | 5.4 | 3.2 | A-1 | 489 | 100 | $1.5 \times 10^{-6}$ | 6.0 | 3.8 |
| Comparative Example 2 | D-13 | 417 | 81 | $1.5 \times 10^{-8}$ | 5.4 | 2.8 | A-1 | 489 | 100 | $1.5 \times 10^{-6}$ | 6.0 | 3.8 |
| Comparative Example 3 | D-14 | 512 | 103 | $1.3 \times 10^{-8}$ | 5.6 | 3.3 | A-1 | 489 | 100 | $1.5 \times 10^{-6}$ | 6.0 | 3.8 |
| Comparative Example 4 | D-1 | 453 | 99 | $8.5 \times 10^{-6}$ | 5.5 | 3.2 | A-15 | 533 | 163 | $1.1 \times 10^{-5}$ | 5.9 | 4.0 |
| Comparative Example 5 | D-1 | 453 | 99 | $8.5 \times 10^{-6}$ | 5.5 | 3.2 | A-16 | 483 | 140 | $2.2 \times 10^{-3}$ | 6.9 | 4.7 |
| Comparative Example 6 | D-1 | 453 | 99 | $8.5 \times 10^{-6}$ | 5.5 | 3.2 | | | | | | |
| Comparative Example 7 | | | | | | | A-1 | 489 | 100 | $1.5 \times 10^{-6}$ | 6.0 | 3.8 |

TABLE 2

| | Maximum absorption wavelength (nm) | Full width at half maximum (nm) | Absorption coefficient at maximum absorption wavelength (cm$^{-1}$) | Maximum sensitivity wavelength (nm) | External quantum efficiency at maximum sensitivity wavelength (%) | Photocurrent value at maximum sensitivity wavelength (A/cm$^2$) | Dark current value (A/cm$^2$) | ON/OFF ratio |
|---|---|---|---|---|---|---|---|---|
| Example 1 | 471 | 98 | $6.41 \times 10^4$ | 460 | 40 | $5.0 \times 10^{-4}$ | $4.9 \times 10^{-6}$ | 101 |
| Example 2 | 455 | 84 | $4.73 \times 10^4$ | 450 | 34 | $1.2 \times 10^{-4}$ | $9.7 \times 10^{-7}$ | 124 |
| Example 3 | 415 | 46 | $5.09 \times 10^4$ | 420 | 36 | $1.8 \times 10^{-4}$ | $1.1 \times 10^{-6}$ | 164 |
| Example 4 | 519 | 95 | $3.08 \times 10^4$ | 520 | 34 | $1.1 \times 10^{-4}$ | $1.2 \times 10^{-6}$ | 92 |
| Example 5 | 421 | 43 | $5.74 \times 10^4$ | 420 | 35 | $1.4 \times 10^{-4}$ | $8.2 \times 10^{-7}$ | 171 |
| Example 6 | 547 | 50 | $5.35 \times 10^4$ | 540 | 41 | $5.1 \times 10^{-4}$ | $4.8 \times 10^{-6}$ | 107 |
| Example 7 | 482 | 63 | $5.26 \times 10^4$ | 480 | 41 | $5.2 \times 10^{-4}$ | $4.1 \times 10^{-6}$ | 127 |
| Example 8 | 459 | 67 | $5.97 \times 10^4$ | 460 | 39 | $4.8 \times 10^{-4}$ | $2.7 \times 10^{-6}$ | 177 |
| Example 9 | 514 | 90 | $1.01 \times 10^3$ | 520 | 50 | $1.0 \times 10^{-3}$ | $1.5 \times 10^{-6}$ | 667 |
| Example 10 | 449 | 87 | $3.99 \times 10^4$ | 450 | 53 | $1.8 \times 10^{-3}$ | $6.7 \times 10^{-6}$ | 268 |
| Example 11 | 488 | 89 | $4.12 \times 10^4$ | 500 | 52 | $1.6 \times 10^{-3}$ | $7.2 \times 10^{-6}$ | 222 |
| Comparative Example 1 | 495 | 151 | $4.37 \times 10^4$ | 490 | 22 | $4.3 \times 10^{-4}$ | $1.4 \times 10^{-4}$ | 4 |
| Comparative Example 2 | 410 | 138 | $6.96 \times 10^4$ | 420 | 15 | $2.6 \times 10^{-4}$ | $1.0 \times 10^{-4}$ | 2 |
| Comparative Example 3 | 483 | 141 | $3.90 \times 10^4$ | 480 | 15 | $3.6 \times 10^{-4}$ | $1.2 \times 10^{-4}$ | 3 |
| Comparative Example 4 | 532 | 193 | $7.28 \times 10^4$ | 540 | 52 | $1.2 \times 10^{-3}$ | $2.5 \times 10^{-5}$ | 47 |
| Comparative Example 5 | 467 | 140 | $8.04 \times 10^4$ | 500 | 1 | $1.3 \times 10^{-4}$ | $1.1 \times 10^{-4}$ | 1 |
| Comparative Example 6 | 453 | 99 | $7.27 \times 10^4$ | 460 | 1 | $1.6 \times 10^{-4}$ | $1.7 \times 10^{-5}$ | 6 |
| Comparative Example 7 | 489 | 105 | $6.51 \times 10^4$ | 460 | 2 | $1.8 \times 10^{-4}$ | $2.6 \times 10^{-5}$ | 12 |

INDUSTRIAL APPLICABILITY

The photoelectric conversion element of the present invention can be applied in a field of an image sensor, solar cells, or the like. Specifically, the photoelectric conversion element can be used in a field of, for example, an image element mounted on a mobile phone, a smartphone, a tablet PC, a digital still camera, or the like; a sensing device of a photovoltaic power generator, a visible light sensor, or the like.

REFERENCE SIGNS

10 First electrode
13 Electron blocking layer
15 Organic layer
17 Hole blocking layer
20 Second electrode
31 Molecule of compound represented by general formula (1)
32 Molecule of compound represented by general formula (2)
33 Molecule of compound having specific skeleton
34 Molecule of compound having different skeleton from that of compound molecule 33
41 Photoelectric conversion element for detecting red light
42 Photoelectric conversion element for detecting green light
43 Photoelectric conversion element for detecting blue light

The invention claimed is:

1. A photoelectric conversion element, comprising:
a first electrode,
a second electrode, and
at least one organic layer being present between the first electrode and the second electrode, wherein the organic layer contains a compound represented by general formula (1), and a compound represented by general formula (2):

wherein

A is a group represented by general formula (3),

B is a group selected from the group consisting of an alkoxy group, an alkylthio group, an aryl ether group, an aryl thioether group, an amino group, a furanyl group, a thiophenyl group, a pyrrolyl group, a benzofuranyl group, a benzothiophenyl group, an indolyl group, a dibenzofuranyl group, a dibenzothiophenyl group, and a carbazolyl group, C is an aromatic heterocyclic group containing an electron-accepting nitrogen, or a group selected from the group consisting of an alkyl group, a cycloalkyl group, an alkenyl group, a cycloalkenyl group, an alkynyl group, an aryl group, and a heteroaryl group, and substituted with a halogen or a cyano group, and each of m and n represents an integer of 1 to 4, and

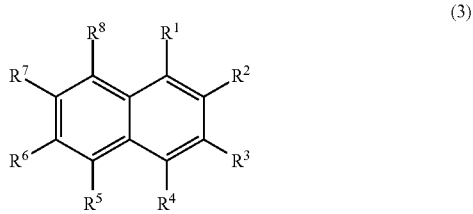

(3)

wherein $R^1$ to $R^8$ may be the same as or different from one another, and are each a group selected from the group consisting of a hydrogen atom, an alkyl group, a cycloalkyl group, an alkenyl group, a cycloalkenyl group, an alkynyl group, and an aryl group, $R^1$ to $R^8$ may form a monocyclic or condensed ring by bonding adjacent groups among $R^1$ to $R^8$ to each other, provided that in general formula (1), B is linked at any m positions of $R^1$ to $R^8$ and a condensed ring formed by bonding any adjacent groups among $R^1$ to $R^8$ to each other, and in general formula (2), C is linked at any n positions of $R^1$ to $R^8$ and a condensed ring formed by bonding any adjacent groups among $R^1$ to $R^8$ to each other, and further provided that in the organic layer A is the same group in the compound of general formula (1) and in the compound of general formula (2).

2. The photoelectric conversion element according to claim 1, wherein adjacent groups among $R^1$ to $R^8$ are bonded to each other in general formula (3), and form a condensed ring including 3 to 6 rings in total.

3. The photoelectric conversion element according to claim 2, wherein general formula (3) has a ring structure selected from among anthracene, phenanthrene, naphthacene, pyrene, chrysene, triphenylene, fluoranthene, benzofluoranthene, perylene, pentacene, and hexacene.

4. The photoelectric conversion element according to claim 2, wherein general formula (3) has a ring structure selected from among anthracene, phenanthrene, naphthacene, pyrene, chrysene, triphenylene, fluoranthene, benzofluoranthene, perylene, and hexacene.

5. The photoelectric conversion element according to claim 2, wherein general formula (3) has a pyrene structure.

6. The photoelectric conversion element according to claim 1, wherein ionization potential ($Ip_1$) and electron affinity ($Ea_1$) of the compound represented by general formula (1), and ionization potential ($Ip_2$) and electron affinity ($Ea_2$) of the compound represented by general formula (2) are $Ip_1 < Ip_2$ and $Ea_1 < Ea_2$.

7. The photoelectric conversion element according to claim 1, wherein difference between the maximum value of an absorption spectrum of the compound represented by general formula (1) and the maximum value of an absorption spectrum of the compound represented by general formula (2) is 50 nm or less.

8. The photoelectric conversion element according to claim 1, wherein a full width at half maximum of an absorption spectrum of the compound represented by general formula (1) and a full width at half maximum of an absorption spectrum of the compound represented by general formula (2) are both 25 nm or more to 100 nm or less.

9. The photoelectric conversion element according to claim 1, wherein the organic layer includes a plurality of layers, and one layer among the layers contains both the compound represented by general formula (1) and the compound represented by general formula (2).

10. The photoelectric conversion element according to claim 9, wherein the layer containing both the compound represented by general formula (1) and the compound represented by general formula (2) among the organic layers is a bulk heterojunction layer by the compounds.

11. The photoelectric conversion element according to claim 9, wherein a mixture ratio of the compound represented by general formula (1) and the compound represented by general formula (2) is 1:3 to 3:1.

12. The photoelectric conversion element according to any claim 1, wherein the organic layer has a film thickness of 20 nm or more to 200 nm or less.

13. The photoelectric conversion element according to claim 1, wherein a voltage application part for applying an electric field to the organic layer is further provided.

14. The photoelectric conversion element according to claim 1, wherein the voltage application part applies an electric field of $10^5$ V/m or more to $10^9$ V/m or less to the organic layer.

15. An image sensor, comprising the photoelectric conversion element according to claim 1.

16. The image sensor according to claim 15, wherein the image sensor includes two or more kinds of photoelectric conversion elements.

17. The image sensor according to claim 16, wherein the two or more kinds of photoelectric conversion elements have a laminated structure.

* * * * *